(12) United States Patent
Peterson

(10) Patent No.: US 6,238,376 B1
(45) Date of Patent: *May 29, 2001

(54) BONDING A POLYMER MEMBER TO A METALLIC MEMBER

(75) Inventor: Eric D. Peterson, Fremont, CA (US)

(73) Assignee: Advanced Cardiovascular Systems, Inc., Santa Clara, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/819,965

(22) Filed: Mar. 18, 1997

(51) Int. Cl.[7] .............................. A61M 5/00; A61M 25/00
(52) U.S. Cl. ..................... 604/264; 604/96.01; 604/523
(58) Field of Search .............................. 604/96, 103, 264, 604/280, 282, 523, 525, 528, 96.01, 915, 921; 138/155; 606/192, 194

(56) References Cited

U.S. PATENT DOCUMENTS

| 4,390,668 | * | 6/1983 | Garver, Sr. ........................ 525/444 |
| 4,419,169 | | 12/1983 | Becker et al. ...................... 156/359 |
| 4,636,272 | | 1/1987 | Riggs ................................. 156/158 |
| 4,877,031 | * | 10/1989 | Conway et al. ..................... 128/344 |
| 5,108,525 | | 4/1992 | Gharibadeh ............................. 156/86 |
| 5,250,069 | * | 10/1993 | Nobuyoshi et al. ................. 606/192 |
| 5,300,025 | * | 4/1994 | Wantink ................................. 604/96 |
| 5,370,616 | * | 12/1994 | Keith et al. ........................... 604/102 |
| 5,480,383 | | 1/1996 | Bagaoisan et al. .................... 604/96 |
| 5,599,326 | * | 2/1997 | Carter ................................... 604/282 |
| 5,743,875 | * | 4/1998 | Sirham et al. ......................... 604/96 |

FOREIGN PATENT DOCUMENTS

| 0 352 955 | 1/1990 | (EP) . |
| 0 513 818 | 11/1992 | (EP) . |
| 2 182 110 | 5/1987 | (GB) . |
| 58-074295 | 5/1983 | (JP) . |
| 08247371 | 9/1996 | (JP) . |
| WO 93/20882 | 10/1993 | (WO) . |
| WO 96/20752 | 7/1996 | (WO) . |

* cited by examiner

Primary Examiner—Sharon Kennedy
Assistant Examiner—LoAn H. Thanh
(74) Attorney, Agent, or Firm—Heller Ehrman White & McAuliffe LLP

(57) ABSTRACT

This invention is directed to a method of bonding thermoplastic catheter parts to a metallic member such as hypotubing and the product formed. The polymeric material is hot pressed against the metallic member with sufficient pressure to ensure plastic deformation of the polymeric material. A fluid tight bond is formed which can withstand pressures of up to 650 psi.

8 Claims, 2 Drawing Sheets

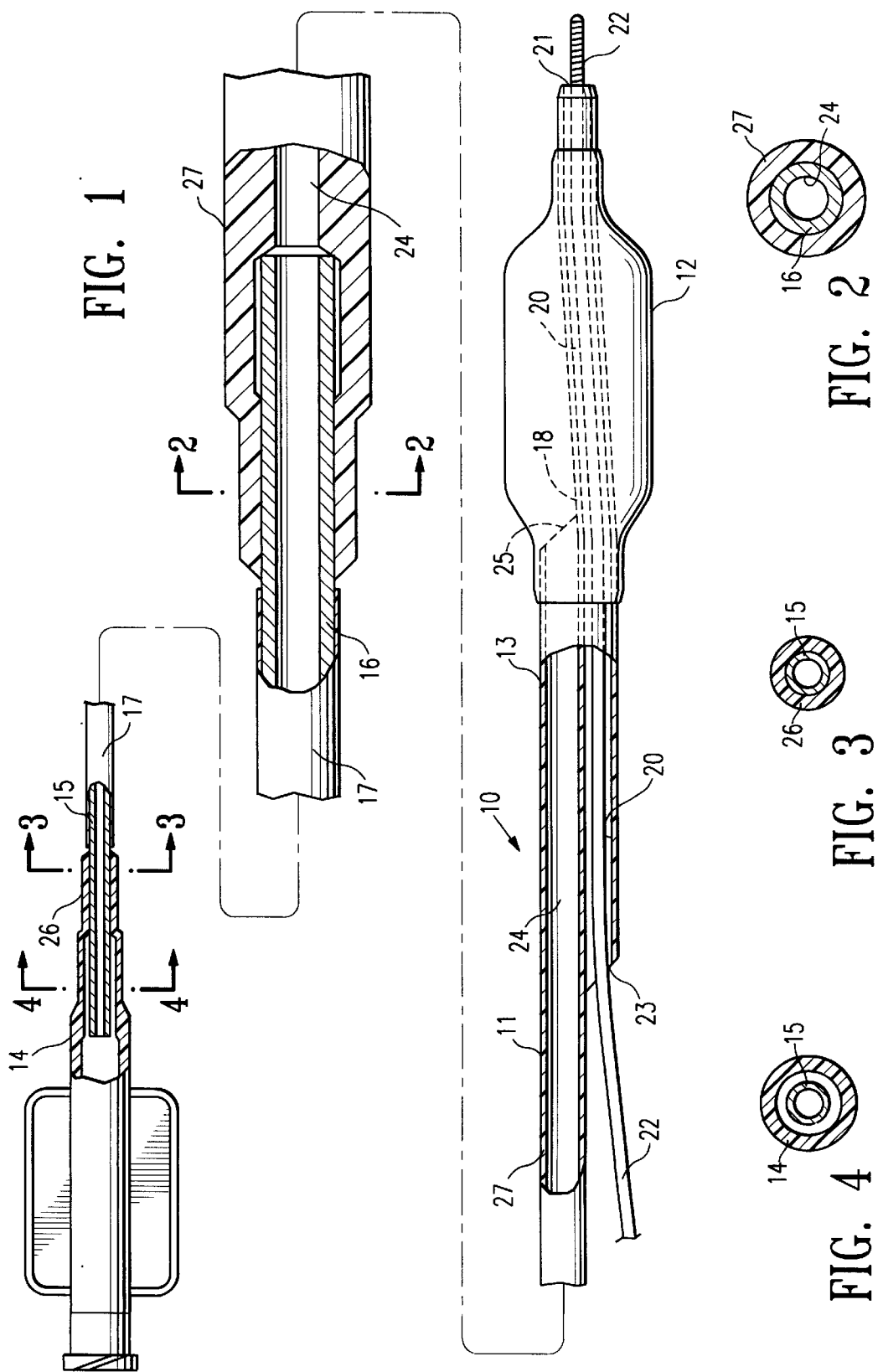

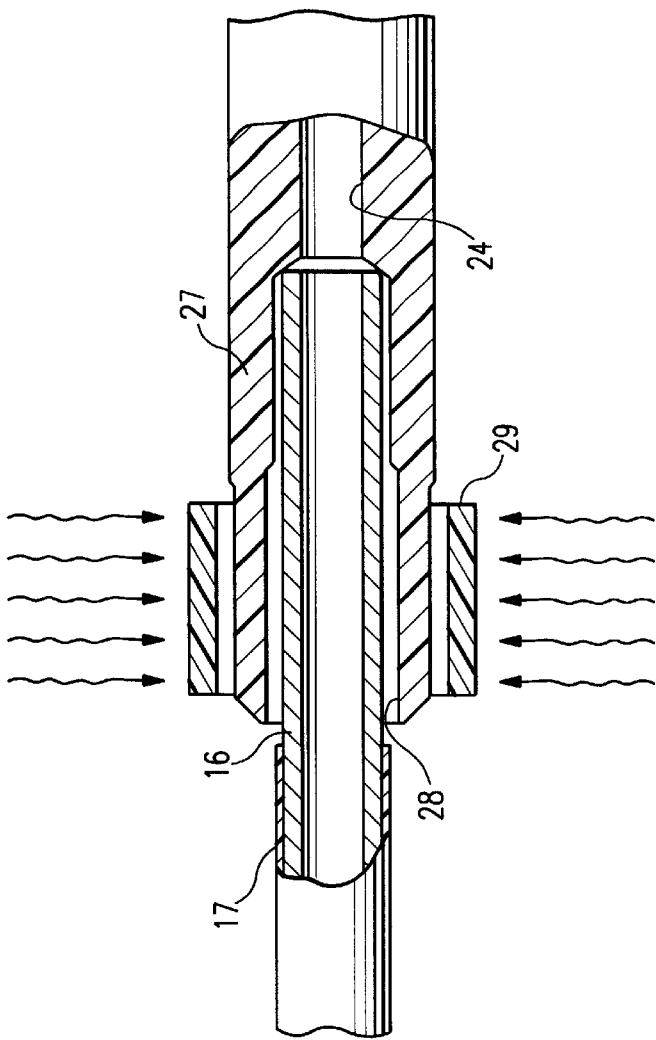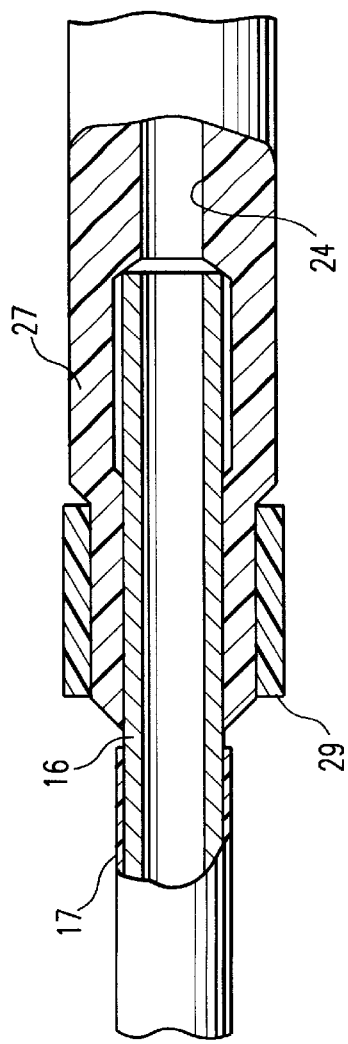

BONDING A POLYMER MEMBER TO A METALLIC MEMBER

BACKGROUND OF THE INVENTION

This invention generally relates to attachment of high strength polymeric members to a metallic member and particularly to the attachment of polymeric tubes to metallic tubes in intravascular devices such as catheters for use in percutaneous transluminal coronary angioplasty (PCTA).

In a typical PTCA procedure a dilatation balloon catheter is advanced over a guidewire to a desired location within the patient's coronary anatomy where the balloon of the dilatation catheter is properly positioned within the stenosis to be dilated. The balloon is then inflated to a predetermined size with radiopaque liquid at relatively high pressures (generally 4–20 atmospheres) to dilate the stenosed region of the diseased artery. One or more inflations may be needed to effectively dilate the stenosis. The catheter may then be withdrawn from the stenosis or advanced further into the patient's coronary anatomy to dilate additional stenoses.

The inflation pressures used in PTCA procedures have increased considerably due to the utilization of high strength balloon materials. However, such higher pressures also place substantial stress on other catheter components and particularly the junctions between various catheter components. Examples of such components and junctions are the adapter and the junction with the proximal end of a metallic hypotube and the adapter and the distal end of a metallic hypotube and the polymeric tubular products which form the distal portion of a rapid exchange type dilatation catheter. Present manufacturing procedures involve the use of adhesives, heat shrinking and the like which limit the materials which can be used and the combination of materials which can be used and which complicate the manufacturing procedure. What has been needed and has heretofore been unavailable is an uncomplicated procedure which produces high strength, hermetically sealed bonds.

SUMMARY OF THE INVENTION

The present invention is directed to a system for securely bonding a high strength polymer material to a metallic member and particularly a small diameter tubular polymeric product to a small diameter tubular metallic product.

In accordance with the invention the polymeric member is disposed in contact with the metallic member, the polymer member is hot pressed against the metallic member at a temperature above the glass transition temperature of the polymeric material but less than the melting point thereof to effect significant plastic deformation of the polymeric material. The result is a high strength bond and a fluid tight seal which will not leak even under high pressures.

One presently preferred embodiment of the invention is directed to the bonding of small diameter tubular polymeric members to small diameter tubular metallic members. A portion of the metallic member is inserted into the inner lumen of a polymeric tubular member and a heat shrinkable collar is disposed about the portion of the polymeric tubular member into which the metallic member is disposed. Heat is applied to the heat shrinkable collar, and the polymeric tubular member, causing the collar to shrink and apply sufficient pressure against the polymeric tubular member to plastically deform it and thereby bond the polymeric material to the surface of the metallic member. The heat shrinkable collar may be left in place or removed from the polymeric tubular member after the bond is formed. A masking layer may be provided between the collar and the polymeric tubular member to prevent bonding and facilitate removal of the collar.

Generally, the polymeric material should be a high strength thermoplastic polymer which is at most semi-crystalline, preferably non-crystalline, and which is not ethylenically cross-linked. The preferred polymeric material is an engineering polymer such as polyetheretherketone (PEEK), e.g. 581G sold by Victrex. Other polymeric materials include polyetheramide sold under the trademark ULTEM by General Electric, polyphenylene sulfide and polysulfone. The metallic member may be stainless steel, such as 304 stainless steel, or a superelastic or pseudoelastic NiTi alloy. Other metallic materials may be used such as titanium and alloys thereof. There is no special surface preparation needed for the metallic members other than removing surface contaminants such as oil, grease and the like.

One of the advantages of the invention is that the bond is strong enough and the seal is sound enough so the number of parts needed to construct an intravascular catheter is reduced considerably. For example, in present conventional manufacturing practices for rapid exchange type catheters, such as the LIFESTREAM Dilatation Catheter sold by Advanced Cardiovascular Systems, Inc., up to five parts are needed to attach a proximal hub or adapter to the proximal end of a hypotube shaft. With the present invention the distal end of the adapter can be bonded directly to the proximal extremity of a hypotube.

In addition to a significant reduction in the number of parts, there is no adhesive used, so there is no requirements for an adhesive curing step to form an adhesive bond. The bond of the present invention between the polymeric material and metallic material is strong, durable and provides a fluid tight seal between the joined parts. These and other advantages of the invention will become more apparent from the following detailed description and the accompanying exemplary drawings.

BRIEF DESCRIPTION OF THE DRAWINGS

FIG. 1 is an elevational view, partially in section, of a rapid exchange type dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 4 is a transverse cross-sectional view of the catheter shown in FIG. 1 taken along the lines 4—4.

FIG. 5 is an enlarged partial elevational view of a polymeric tubular member in position to be hot pressed against the metallic tubular member to facilitate the bonding therebetween.

FIG. 6 is a longitudinal cross-sectional view of the members shown in FIG. 5 after the boding procedure.

DETAILED DESCRIPTION OF THE INVENTION

FIGS. 1–5 illustrate a rapid exchange type balloon dilatation catheter 10 which has an elongated shaft 11 with a dilatation balloon 12 on a distal shaft section 13 of the shaft and an adapter 14 on the proximal end of the proximal shaft section 15. The proximal shaft 15 is formed of a metallic hypotube 16 with a lubricious coating 17. The distal shaft section 13 includes a distally extending tubular member 18 which has a guidewire receiving inner lumen 20 and which extends through the interior of the balloon 12 to the port 21 in the distal end of the catheter. A guidewire 22 is shown disposed within the lumen 20 and extending out the distal port 21 and the proximal port 23. The inflation lumen 24 is in fluid communication with the interior of dilatation balloon 12 through inflation port 25.

The distal extremity 26 of the adapter 14 is hot pressed bonded to the proximal extremity of the proximal shaft section 15 in accordance with the invention. A high strength polymeric tubular extension 27 is hot press bonded to the distal extremity of the proximal shaft section 15 in the same manner as the distal extremity of the adapter is bonded to the proximal extremity of the proximal shaft section. In both cases the coating 17 is removed from the exterior of the hypotube 16 to facilitate direct bonding to the metallic surface.

FIGS. 5 and 6 illustrate a presently preferred method of bonding the polymeric member, tubular extension 27 to the metallic tubular member 16. As shown in FIG. 5, the distal end of the metallic tubular member 16 is inserted into the inner lumen 28 of the tubular extension 27. A heat shrinkable tubular collar 29 is disposed about the proximal extremity of the tubular extension 27 and heated to heat shrink temperatures to press the proximal extremity against the exposed surface of the tubular member 16. With the high temperatures and the pressures applied, the proximal extremity is plastically deformed and is securely bonded to the metallic surface. The distal extremity of the adapter 14 is bonded to the proximal extremity of the proximal shaft section in essentially the same manner.

EXAMPLE

A stainless steel hypotube with an outer diameter of 0.024 inch (0.6 mm) and inner diameter of 0.016 inch (0.4 mm) was inserted into the inner lumen of a polymeric tubular member form of polyetheretherketone (PEEK). The inner lumen of the polymeric tubular member was about 0.026 inch (0.7 mm) and the outer diameter was about 0.035 inch (0.9 mm). A short piece of a heat shrinkable tubular FEP with an outer diameter of about 0.077 inch (2 mm) and an inner diameter of about 0.055 inch (1.4 mm) was disposed about the exterior of the polymeric tubular member. The assembly was subjected to an air stream at 450° F.(232° C.) until the tubing becomes cloudy. Upon cooling, the FEP tubular collar was removed. The bond between the PEEK member and the stainless steel member was sound and leak free at internal pressures of up to 650 psi.

Although individual features of embodiments of the invention may be shown in some of the drawings and not in others, those skilled in the art will recognize that individual features of one embodiment of the invention can be combined with any or all the features of one or more of the other embodiments.

What is claimed is:

1. An intravascular catheter with an elongated shaft comprising:
   a) an elongated metallic tubular member having proximal and distal ends and an inner lumen extending between the proximal and distal ends; and
   b) a polymeric tubular member having proximal and distal ends and an inner lumen extending between the proximal and distal ends, in contact with and bonded to a surface of the metallic tubular member by a hot pressed bond between one part of the metallic tubular member and one part of the polymeric tubular member, the polymeric tubular member having a deformed section defined by the hot pressed bond with an outer diameter, and a nondeformed section longitudinally adjacent to the deformed section with a larger outer diameter than the deformed section outer diameter.

2. The intravascular catheter of claim 1 wherein the polymeric material is a thermoplastic polymer selected from the group consisting of polyetheretherketone, polyetheramide, polyphenylene sulfide and polysulfone.

3. The intravascular catheter of claim 1 wherein one end of the polymeric tubular member is disposed about and hot press bonded to the exterior of one end of the metallic tubular member.

4. An intravascular catheter with an elongated shaft comprising:
   a) an elongated metallic tubular member having proximal and distal ends and an inner lumen extending between the proximal and distal ends; and
   b) a polymeric adapter having proximal and distal ends and an inner lumen extending between the proximal and distal ends, in contact with and bonded to a surface of the metallic tubular member by a hot pressed bond between the proximal end of the metallic tubular member and the distal end of the polymeric adapter, the polymeric tubular member having a deformed section defined by the hot pressed bond with an outer diameter, and a nondeformed section longitudinally adjacent to the deformed section with a larger outer diameter than the deformed section outer diameter.

5. The intravascular catheter of claim 4 wherein the distal end of the polymeric adapter is bonded to the exterior of the proximal end of the metallic tubular member.

6. The intravascular catheter of claim 5 wherein the inner lumen of the metallic tubular member is in fluid communication with the inner lumen of the adapter.

7. A balloon catheter comprising:
   a) an elongated proximal shaft section formed at least in part of a metallic tubular member having proximal and distal ends and an inner lumen extending between the proximal and distal ends;
   b) an elongated distal shaft section formed at least in part of a polymeric tubular member having proximal and distal ends and an inner lumen extending between the proximal and distal ends, in contact with and bonded to a surface of the metallic tubular member by a hot pressed bond between part of the metallic tubular member and part of the polymeric tubular member, the polymeric tubular member having a deformed section defined by the hot pressed bond with an outer diameter, and a nondeformed section longitudinally adjacent to the deformed section with a larger outer diameter than the deformed section outer diameter; and
   c) an inflatable balloon on the distal shaft section having an interior in fluid communication with the inner lumen of the polymeric tubular member.

8. A rapid exchange type balloon catheter comprising:
   a) an elongated proximal shaft section formed at least in part of a metallic tubular member having proximal and distal ends and a first inner lumen extending therein; and
   b) an elongated distal shaft section, which is formed at least in part of a polymeric tubular member, having proximal and distal ends, a first port in the distal end and a second port spaced proximal to the distal end, a balloon on the distal shaft section and with an interior, a second inner lumen extending therein which is in fluid communication with the first inner lumen in the metallic tubular member and the interior of the balloon and a third inner lumen which is in fluid communication with the first and second ports, the polymeric tubular member being in contact with and bonded to a surface of the metallic tubular member by a hot pressed bond between part of the metallic tubular member and part of the polymeric tubular member, the polymeric tubular member having a deformed section defined by the hot pressed bond with an outer diameter, and a nondeformed section longitudinally adjacent to the deformed section with a larger outer diameter than the deformed section outer diameter.

* * * * *

UNITED STATES PATENT AND TRADEMARK OFFICE
CERTIFICATE OF CORRECTION

PATENT NO.    : 6,238,376 B1
DATED         : May 29, 2001
INVENTOR(S)   : Eric D. Peterson It is certified that error appears in the above-identified patent and that said Letters Patent is hereby corrected as shown below:

Column 4,
Line 2, after "section", add -- which is distally and --.
Line 22, delete "proximal end of".
Line 23, delete "distal end of".
Line 23, after "adapter,", add -- wherein --.
Line 25, change "tubular member", to read -- adapter --.
Line 25, change "having", to read -- has --.
Line 27, after "section", add -- which is distally and --.
Line 50, after "section", add -- which is distally and --.

Column 6,
Line 3, after "section", add -- which is distally and --.

Signed and Sealed this

Tenth Day of December, 2002

JAMES E. ROGAN
*Director of the United States Patent and Trademark Office*